United States Patent
Gmachl et al.

(10) Patent No.: US 6,882,675 B2
(45) Date of Patent: Apr. 19, 2005

(54) OPTICAL RESONATORS THAT INCLUDE CHAOTIC RAY PATHS

(75) Inventors: Claire F. Gmachl, New Providence, NJ (US); Evgueni E. Narimanov, Princeton, NJ (US)

(73) Assignee: Lucent Technologies Inc., Murray Hill, NJ (US)

( * ) Notice: Subject to any disclaimer, the term of this patent is extended or adjusted under 35 U.S.C. 154(b) by 108 days.

(21) Appl. No.: 10/413,820

(22) Filed: Apr. 15, 2003

(65) Prior Publication Data

US 2004/0208220 A1 Oct. 21, 2004

(51) Int. Cl.[7] ................................................. H01S 3/08
(52) U.S. Cl. .............................. 372/92; 372/93; 372/94; 372/95; 372/108
(58) Field of Search .............................. 372/92–95, 108

(56) References Cited

U.S. PATENT DOCUMENTS 6,134,257 A * 10/2000 Capasso et al. ................ 372/94

OTHER PUBLICATIONS

Nockel et al. "Ray and wave chaos in asymmetic resonant optical cavities." Nature, vol. 385, pp. 45–57 (Jan. 1997).*
Narimanov. "Semiclassical theory of the emission properties of wave–chaotic resonant cavities." Phys. Rev. Lett., vol. 83, No. 24, pp. 4991–4994 (Dec. 1999).*
D. Horn et al., *2.5–km Low–Temperature* . . . , Appl. Opt., vol. 10, No. 8, pp. 1892–1898 (Aug. 1971).
J. U. Noeckel et al., *Q spoiling* . . . , Opt. Lett., vol. 19, No. 21, pp. 1693–1695 (Nov. 1994).
J. U. Noeckel et al., *Directional emission* . . . , Opt. Lett., vol. 21, No. 19, pp. 1609–1611 (Oct. 1996).
J. U. Noeckel et al., *Ray and wave chaos* . . . , Nature, vol. 385, pp. 45–47 (Jan. 1997).

G. Hackenbroich et al., *Quantum perturbation* . . . , Phys. Rev. E, vol. 57, No. 1, pp. R5–R8 (Jan. 1998).
C. Gmachl et al., *High–Power Directional* . . . , Science, vol. 280, pp. 1556–1564 (Jun. 1998).
E. E. Narimanov et al., *Semiclassical Theory* . . . , Phys. Rev. Lett., vol. 83, No. 24 pp. 4991–4994 (Dec. 1999).
J. U. Noeckel et al., *Chaotic Light: A Theory of Asymmetric Resonant Cavities,* Ch. 11, "Optical Processes in Microcavities", ed. R. K. Chang et al., World Science Pub (1995) [no copy enclosed].

* cited by examiner

*Primary Examiner*—Don Wong
*Assistant Examiner*—Leith Al-Nazer

(57) ABSTRACT

A compact optical resonator that exhibits long TOPLs is fabricated by (a) selecting a 3-dimensional (3D) reflective, essentially closed surface such that the paths of optical rays that reflect from the interior of the surface include chaotic, open paths; (b) determining the phase-space of the reflection points of the rays; (c) within the phase-space identifying at least one forbidden zone where there are no such reflection points and at least one allowed zone where there is a multiplicity of such reflection points; (d) forming the surface inside a rigid body; and (e) forming at least one physical feature that communicates with the interior of the resonator and is located in a region of the surface that is determined by the positions of the forbidden zones, the allowed zones, or both. In a preferred embodiment physical features such as gas ports are located in regions of the surface that, in phase space, correspond to forbidden zones (so that the circulating optical rays cannot escape via the gas ports). In contrast, physical features such as optical ports are located in regions of the surface that, in phase space, correspond to allowed zones (so that the circulating rays can reach a very long TOPL and then exit from the resonator). In a preferred embodiment, the 3D surface is formed by revolution of a 2D surface about a predetermined axis. Illustratively, the 2D surface has the shape of a quadrupole. Other aspherical shapes of the resonator surface can also be utilized. Application of the resonator to trace-gas sensing systems and to optical amplifiers is also described.

21 Claims, 3 Drawing Sheets

OPTICAL RESONATORS THAT INCLUDE CHAOTIC RAY PATHS

BACKGROUND OF THE INVENTION

1. Field of the Invention

This invention relates to optical resonators and, more particularly, to such resonators that are designed to include chaotic optical ray paths (either fully chaotic or quasi-chaotic ray paths) and, in addition, to the use of such resonators in conjunction with lasers for trace-gas (e.g., pollution) monitoring or optical amplification.

2. Discussion of the Related Art

Optical cavity resonators are devices having internal optical path lengths that are much longer than their physical dimensions. The long optical path lengths are produced by multiple reflections of optical rays at mirror surfaces. Cavity resonators find widespread application in diverse fields; for example, in amplifiers for high power laser systems and in ultra-high sensitivity gas sensing systems.

In the case of atmospheric pollution sensors, for example, a sample of polluted air is introduced into a chamber, and a light beam of suitable wavelength is passed through the sample. The wavelength is chosen to correspond to an absorption band/line of the particular pollutant that is suspected to be in the atmosphere. However, because such pollutants are often present in trace amounts, the amount of absorption in a single pass of the beam is extremely small and, in fact, is often not above the noise level of the detection system. To be detected with a sufficient signal-to-noise ratio the amplitude modulation of the beam produced by the trace-gas absorption must be greater than the background noise, which is nearly impossible to achieve in a single pass. Consequently, the prior art has resorted to the use of an optical cavity resonator to contain the sample so that absorption by the trace pollutant can take place on each of a multiplicity of passes of the beam through the sample.

Typically, a total optical path length (TOPL) from about several meters to a few hundred meters or a few kilometers is desired for the detection of many trace gases (e.g., CO, $NO_x$, $NH_3$, $CH_4$, their isotopes, water vapor isotopes, and others) in the atmosphere at signal-to-noise ratios of at least 2 or at a sensitivity level of few parts per billion. However, to achieve such TOPLs the prior art has resorted to resonators that have very large physical dimensions; e.g., the resonator described by D. Horn et al. [*Appl. Opt. Vol.* 10, No. 8, pp. 1892–1898, (1971)] utilized 254 reflections along a 10 m base path for a TOPL of 2.54 km. Such designs pose several problems. First, the number of reflections is limited by the presence of various ports (e.g., gas ports, optical ports) that interrupt the reflective surfaces. Second, the TOPL of 2.54 km was achieved only with an unwieldy, 10-m-long apparatus. Third, long apparatus of this type typically has low gas throughput.

Consequently, there is a need in the trace-gas sensing art for a more compact optical cavity resonator that can achieve the relatively long TOPLS necessary for trace gas monitoring. Advantageously, the compactness of the resonator would also provide for a relatively rapid gas cycle time.

Resonators with long TOPLs also find application in optical amplifiers for high power laser systems. A signal laser beam to be amplified is injected into a resonator that contains a gain medium. The beam undergoes multiple reflections within the resonator. Therefore, the longer the TOPL traversed by the beam, the higher the total gain it experiences. However, if the injected beam traverses a closed path, it will eventually deplete the gain medium, reducing its ability to provide gain. This phenomenon is sometimes referred to as gain depletion.

Thus, a need remains in the optical amplifier art for a resonator that is compact, yet has a relatively long TOPL, and that exhibits open paths so that the gain medium does not exhibit gain depletion to any significant extent.

BRIEF SUMMARY OF THE INVENTION

In accordance with one aspect of our invention, a compact optical resonator that exhibits long TOPLs is fabricated by (a) selecting a 3-dimensional (3D) reflective, essentially closed surface such that the paths of optical rays that reflect from the interior of the surface include chaotic open paths; (b) determining the phase-space of the reflection points of the rays; (c) within the phase-space identifying at least one forbidden zone where there are no such reflection points and at least one allowed zone where there is a multiplicity of such reflection points; (d) forming the surface inside a rigid body; and (e) forming at least one physical feature that communicates with the interior of the resonator and is located in a region of the surface that is determined by the positions of the forbidden zones, the allowed zones, or both. In a preferred embodiment physical features such as gas ports are located in regions of the surface that, in phase space, correspond to forbidden zones (so that the circulating optical rays cannot escape via the gas ports). In contrast, physical features such as optical ports are located in regions of the surface that, in phase space, correspond to allowed zones (so that the circulating rays can reach a very long TOPL and then exit from the resonator). In a preferred embodiment, the 3D surface is formed by revolution of a 2D surface about a predetermined axis. Illustratively, the 2D surface has the shape of a quadrupole. Other aspherical shapes of the resonator surface can also be utilized.

In accordance with one illustrative embodiment of our invention the revolution of a quadrupole forms a cavity resonator within a rigid body, with the physical length of the resonator being only few centimeters (e.g., about 10–50 cm) long. Yet, we have calculated that even with such short resonators, we can achieve TOPLs in the range of several hundred meters to about 1 km.

Resonators in accordance with our invention are particularly well suited to applications in the field of trace gas sensing and optical amplification, both of which exploit two features of our resonators: long TOPLs and open paths.

BRIEF DESCRIPTION OF THE SEVERAL VIEWS OF THE DRAWING

Our invention, together with its various features and advantages, can be readily understood from the following more detailed description taken in conjunction with the accompanying drawing, in which.

DETAILED DESCRIPTION OF THE INVENTION

Glossary

Figure 1:
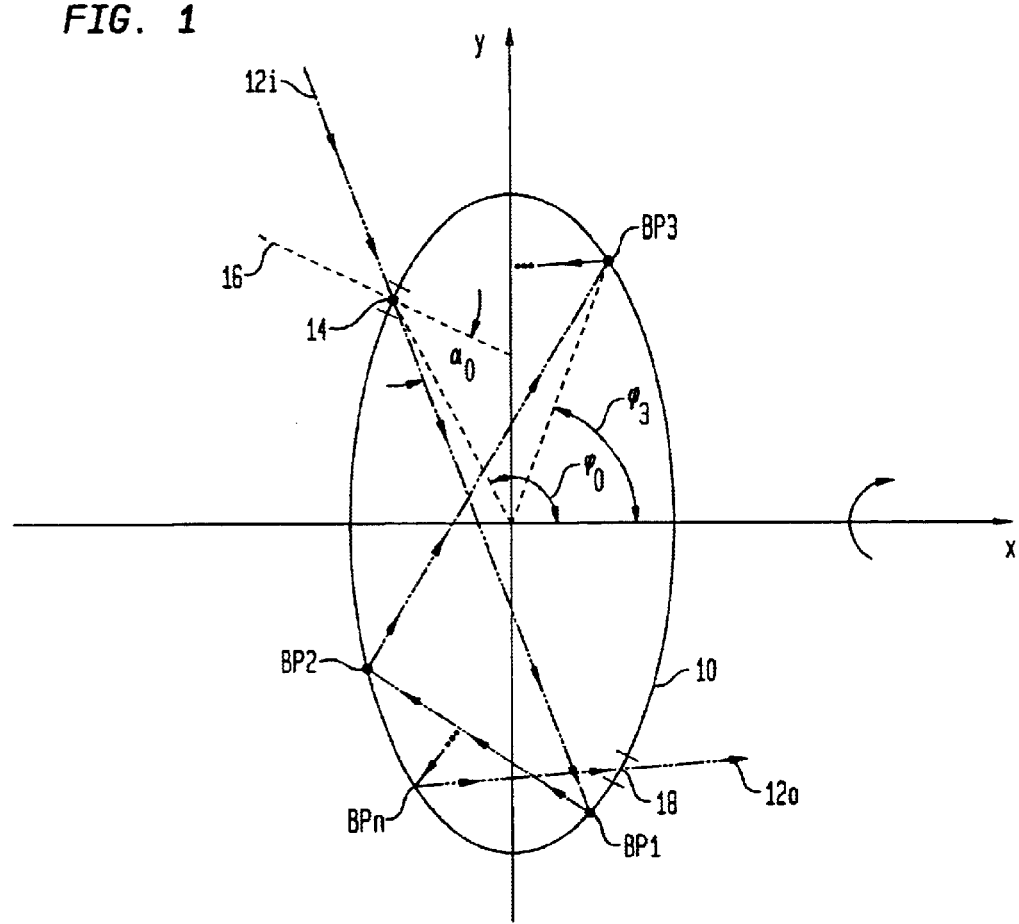
FIG. 1 is a schematic view of a 2D quadrupole, which, when rotated about the x-axis, forms a surface of revolution of an optical resonator that may include either fully chaotic or partially chaotic optical ray paths in accordance with one embodiment of our invention. The dimension of the quadrupole in the x-direction may be either shorter (as shown in FIG. 1) or longer than the dimension of the quadrupole in the y-direction. This figure illustrates various parameters (polar coordinate $\phi_0$ in the x-y plane, and entrance angle $\alpha_0$ with respect to the surface normal 16) that are used to calculate the phase space of reflection points of optical rays incident on the surface.

The terms defined below are used in the description of various embodiments of our invention.

Bounce Points: Bounce points (also known as reflection points) are the points on the interior surface of a resonator where optical rays are reflected.

Forbidden and Allowed Zones: A forbidden zone (FZ) is a region on the interior surface of a resonator that never experiences any reflections of an optical ray that traverses a particular type of ray path [i.e., a chaotic ray path, a regular ray path (as defined below), or both]. A FZ, therefore, has no bounce points for such rays. In contrast, an allowed zone (AZ) in theory experiences at least one reflection and, therefore, has at least one bounce point for rays that traverse one of the particular types of ray paths. In practice an AZ has a multiplicity of bounce points, but their density may vary from one region of the AZ to another.

In the phase space (defined below) of diagram of FIG. 3 we show several regions that may correspond to FZs and AZs depending on the conditions discussed below. Thus, region 32 illustrates a relatively large FZ for rays that traverse either chaotic or regular ray paths; region 34a illustrates a relatively smaller FZ (outside the annulus 34b and between the six small ovals 34c); and the central region of the annulus 34b, as well as the central regions of ovals 34c, also illustrate smaller FZs. On the other hand, region 30 illustrates an AZ for rays that traverse chaotic ray paths. Conversely, for rays that traverse regular ray paths, regions 30 and 32 are both FZs, whereas all 1D lines (e.g., 31) and islands (e.g., 33, 36) are AZs.

The location of a FZ is determined by the shape of the resonator surface and initial direction ($\alpha_0$, $\beta_0$) of the input rays (beam). These initial conditions are not isolated values. Rather, they represent continuous intervals of the angle pairs ($\alpha_0$, $\beta_0$). That is, due to the wave nature of light, it is not possible to inject a beam into a single path; it will always enter as a group of paths that form a beam.

Note, if a zone is forbidden for a particular interval of initial conditions, it will have no bounce points regardless of whether the ray path is chaotic or regular, as defined below.

Chaotic Ray Paths: A chaotic ray path (also known as a chaotic ray trajectory) is defined as a path followed by any two optical rays, which, despite having infinitesimally close initial conditions (i.e., with an arbitrarily small difference between either their starting points or starting directions), increasingly deviate from one another as time progresses until their path separation is much larger than their initial separation.

A signature of the chaotic path: its bounce points are not confined to a one-dimensional line in phase space (defined below). As illustrated in FIG. 3, one-dimensional lines include both lines that do not close (e.g., the triangle-like curved lines in region 31) and lines that do close (e.g., the egg-like lines in region 33, the ellipse-like lines in region 34, and others), also known as islands. Instead, a chaotic ray path has bounce points throughout the entire "grainy" two-dimensional region 30 (also known as the chaotic sea). Every dot of FIG. 3 is a single bounce point; some dots lie so close together that they blend to form one-dimensional lines, as discussed above. However, dots that are adjacent one another in phase space need not be adjacent one another in time (or in bounce sequence); that is, a ray may experience other reflections before it propagates in phase space from one dot to an adjacent dot.

Regular Ray Paths; A regular ray path is a path that is not a chaotic ray path in the sense defined above. Whether a ray path is regular or chaotic depends on the shape of the resonator surface and the angle at which the ray is directed into the resonator.

A signature of the regular path: they are confined to bounce points that form islands or open one-dimensional lines, also described above. Each island may enclose another, smaller island. The two islands define a region between them as well as a region enclosed by the smaller island. Similarly, a pair of spaced-apart one-dimensional lines defines an interstitial region between them.

An interstitial region is a FZ for rays that have initial conditions outside the boundary of the particular region. For example, the interior of an island would be a FZ for rays that have initial conditions that lie outside the island. On the other hand, an interstitial region is an AZ for rays that have initial conditions that lie inside the boundary of the particular region. For example, the interior of an island would be an AZ for rays that have initial conditions that lie inside the boundary of the island. The paths of such rays would trace out a multiplicity of additional islands nested within one another and within the original island (e.g., as shown by the islands 33 and 36 of FIG. 3).

Finally, we note that interstitial regions may contain a mixture of chaotic and regular ray paths, which exist in quasi-chaotic resonators, as defined below.

Fully vs. Quasi-Chaotic Resonators: Chaotic resonators are either fully chaotic or partially chaotic (also known as quasi-chaotic). A fully chaotic resonator is a resonator that allows only chaotic ray paths for all initial conditions, and a quasi-chaotic resonator is a resonator that allows both chaotic and regular ray paths depending on the particular initial conditions selected.

Phase Space: The phase space of a resonator is a representation of the location of bounce points of optical rays as a function of the angle the rays enter the resonator and the polar coordinates of their bounce points. FIG. 3 depicts an exemplary 2D projection of the phase space diagram (also known as a surface-of-section plot) of a 3D quasi-chaotic resonator with axial symmetry (e.g., a surface of revolution) with respect to the y-axis. FIG. 3 is for discussion purposes only, the actual shape of the resonator surface is unspecified.

The figure is used to understand how a quasi-chaotic resonator can provide long TOPLs; the graph is valid for a certain set of incidence angles ($\alpha_0$, $\beta_0$) that correspond to optical rays having a particular relative angular momentum (equal to 0.3 in this case) with respect to the axis of symmetry. The angular momentum in this context is set by the choice of ($\alpha_0$, $\beta_0$) and roughly describes the rate of revolution of the optical beam path around a chosen axis, typically the symmetry axis of the resonator (if one is present). Other resonator shapes, which need not have an axis of symmetry, are also suitable for use in our invention as long as they are not perfect spheres.

Figure 3:
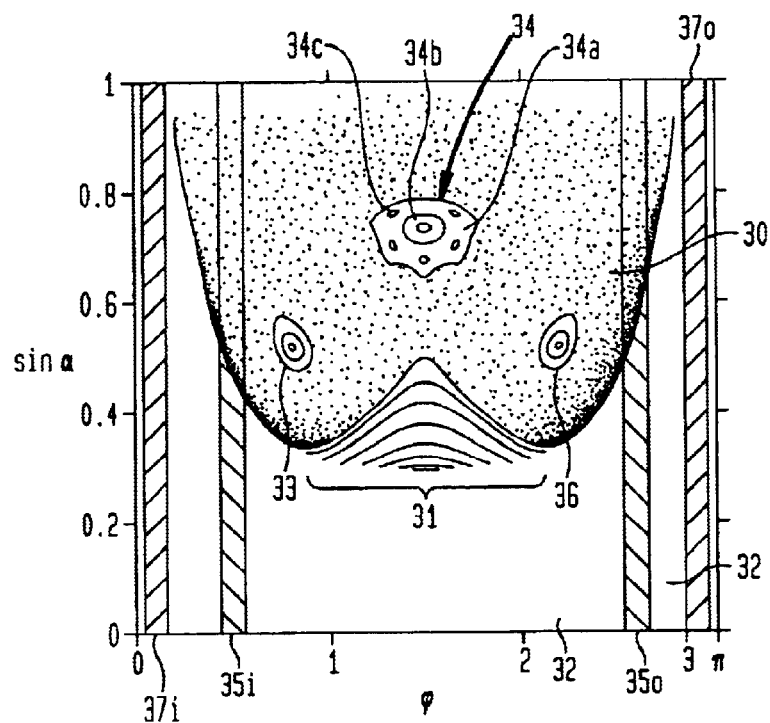
FIG. 3 depicts an exemplary 2D projection of the phase space diagram of a 3D resonator in which the dimension of the resonator along the axis of rotation is longer than the dimension of the resonator in the direction perpendicular to the axis of rotation.

In contrast, the phase space for a fully chaotic resonator would exhibit no 1D lines or islands, but it would have a chaotic sea 30 and a FZ 32 of the type depicted in FIG. 3.

Note, although FIG. 1 demonstrates axial symmetry with respect to the x-axis, its phase space follows the underlying principles discussed above.

Prior Art: Chaotic and regular paths are described by J. U. Noeckel et al. in several journal articles: *Nature*, Vol. 385, No. 6611, pp. 45–47 (1997), *Opt. Lett.*, Vol. 21, No. 19, pp. 1609–1611 (1996), and *Opt. Lett.*, Vol. 19, No. 21, pp. 1693–1695 (1994), and by E. Narimanov et al, *Phys. Rev. Lett.*, Vol. 83, No. 24, pp. 4991–4994 (1999), G. Hackenbroich et al, *Phys. Rev. E*, Vol. 57, No. 1, pp. R5-R8 (1998), C. Gmachl et al., *Science*, Vol. 280, pp. 1556–1564 (1998), and F. Capasso et al., U.S. Pat. No. 6,134,257 (2000), all of which are incorporated herein by reference.

Closed vs. Open Ray Paths

Ray paths in our resonators are known as open paths; that is, they do not ever close upon themselves. Closed paths, which always close upon themselves, would lead to inefficient coupling of light out of our resonator and hence degradation of performance. In contrast, closed paths are essential for a laser resonator; e.g., of the type described by the Capasso et al. patent, supra.

General Structure:

With reference now to FIG. 1, we show a 2D essentially closed surface 10; that is, closed except for the possible presence of ports that provide ingress and/or egress from the interior/exterior of the surface. The interior of the surface 10 is highly reflective at the wavelength of optical rays that enter (e.g., rays 12i) the closed surface through an optical port 14 and exit (e.g., rays 12o) through an optical port 18.

A typical optical ray 12i enters the input port 14 at angles $\alpha_0$ (FIG. 1) and $\beta_0$ (FIG. 2), both measured with respect to the surface normal 16. The input port is located at particular polar coordinates ($\phi_0$, $\theta_0$) and has been positioned in accordance with the particular shape of surface 10, as will be discussed hereinafter in accordance with one aspect of our invention. A 3D surface can then be formed by revolution of the 2D-surface about a predetermined axis. Of course, when revolving the 2D surface 10, any ports would not also be revolved; that is, in designing the resonator, the 2D surface itself is first revolved and then the ports are positioned. Our invention, however, is not limited to surfaces of revolution; any aspherical surface is suitable.

Figure 2:
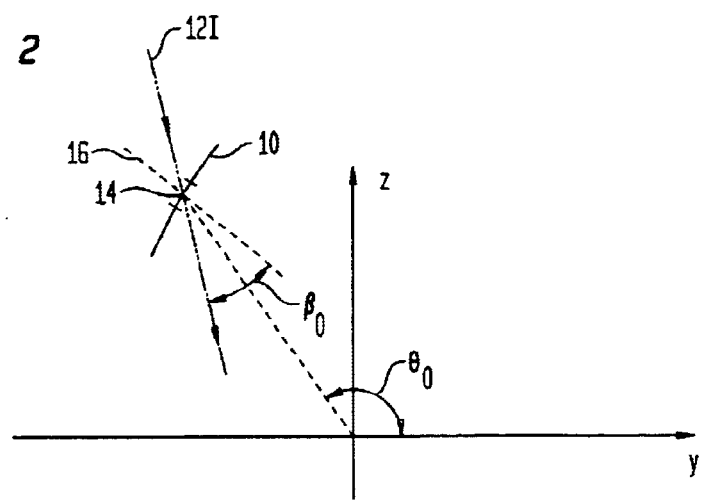
FIG. 2 is a graph depicting the entrance angle $\beta_0$ with respect to the surface normal 16 and the corresponding polar coordinate $\theta_0$ in the y-z plane.

Once a ray enters the optical input port 14, it undergoes a multiplicity n of reflections at the surface 10 and then exits through optical output port 18. The ray paths are chaotic (either fully chaotic or quasi-chaotic) depending on the shape of the surface and the initial (entrance) direction. In 2D the bounce points (BP1, BP2 . . . BPn) of these reflections are designated by the polar coordinate $\phi_i$, i=1, 2, . . . ; in 3D, however, they are designated by a pair of polar coordinates ($\phi_i$, $\theta_i$). For the entrance ray 12i, the entrance angle $\alpha_0$ is shown in FIG. 1; whereas, the entrance angle $\beta_0$ is shown in FIG. 2.

Trace-gas sensing apparatus in accordance with our invention exploits the use of a chaotic resonator to contain a gaseous atmosphere that is suspected to include a particular trace gas (e.g., a pollutant) or a plurality of such trace gases. Several features of our invention enable a relatively large TOPL to be achieved with a relatively short resonator (physical) length, in contrast with prior art devices of this type. First, optical rays in our chaotic resonator design experience a relatively large number of bounce points (e.g., n~1000) without interference by physical features (e.g., ports) and before they exit the resonator. Second, the short physical length enables our apparatus to be much more compact than the prior art. Third, the phase space of our resonator exhibits both AZs and FZs, which enable us to position certain physical features (e.g., gas ports) so that they do not interfere with the circulating rays and other physical features (e.g., optical ports) so that rays exit the resonator only after undergoing many reflections (e.g., n~1000).

The actual position of such FZs and AZs in phase space, as well as in physical space, depends on the particular shape of the resonator surface, on the particular input angles of the entering rays, and on type of ray path launched (chaotic vs. regular). Take for example region 32 of FIG. 3, which includes all of the white area under U-shaped chaotic sea 30, not excluding the areas under the crossed-hatched strips 35o, 35i, 37o and 37i. Region 32 is a FZ for both chaotic and regular rays. In contrast, the grainy area of region 30 is an AZ for chaotic rays, but a FZ for regular rays. On the other hand island 33 (or 36) is an FZ for chaotic rays that have starting (or initial) conditions that lie outside its largest oval, but is an AZ for regular rays that have starting conditions that lie inside its largest oval.

In accordance with one embodiment of our invention, gas ports are located in regions of the surface that correspond to FZs. In this fashion, undesirable escape of rays from the gas ports, which would reduce the detection signal, is effectively avoided. Since zone 32 is much larger than any other FZ illustrated in FIG. 3, it is the preferred FZ location for gas ports. In addition, within FZ 32 we prefer to position the gas ports near the axis of rotation; i.e., near $\phi=0$ and/or near $\phi=\pi$. These locations provide more tolerance for manufacturing uncertainties that might otherwise cause the as-designed gas port to actually overlap an AZ. Zone 32 is a preferred FZ for both chaotic and regular rays. In the phase space of FIG. 3, the strips 37i and 37o illustrate the location of input and output gas ports, respectively. In physical space these ports are designated 67i and 67o in FIGS. 4–6. Alternatively, if the input rays are launched as regular rays, then the gas ports may be located in zone 30.

In accordance with another embodiment of our invention, optical ports are located in regions of the surface that include AZs. In a chaotic or quasi-chaotic resonator, when the input ray is directed along a chaotic path, the optical ports should be located in regions of the surface that correspond to areas of the chaotic sea region 30. In the phase space of FIG. 3 the strips 35i and 35o illustrate the location of input and output optical ports, respectively. In physical space these optical ports are designated 65i and 65o, respectively, in FIGS. 4–6. On the other hand, when the input ray is directed along a regular path, the optical ports should be located in regions of the surface that overlap islands (e.g., 33 and 36 of FIG. 3). The corresponding strips are not shown in FIG. 3, but would simply entail strip 35i being translated to the right until it overlaps island 33 and strip 35o being translated to the left until it overlaps island 36.

Preferred Embodiment

In a preferred embodiment of our invention, the cavity resonator is formed by a 3D closed surface having a predetermined shape that would depend on the particular application; e.g., the 3D surface may be formed by revolution of a 2D surface. In one case, the latter is illustrated by a quadrupole 10 of the type shown in FIG. 1.

Figure 4:
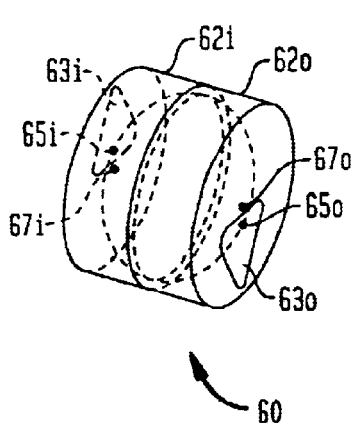
FIG. 4 is an isometric view of an optical resonator in which the dimension of the resonator along the axis of rotation is shorter than the dimension of the resonator in the direction perpendicular to the axis of rotation, in accordance with one embodiment of our invention.
Figure 5:
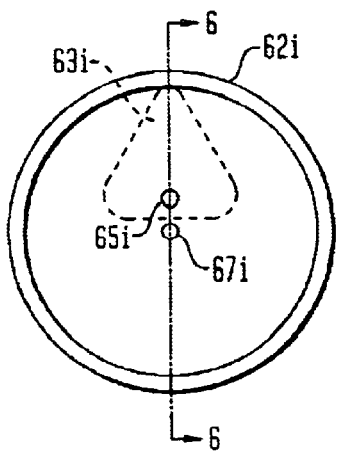
FIG. 5 is an end view of FIG. 4 showing the location of a gas port 67i and an optical port 65i.
Figure 6:
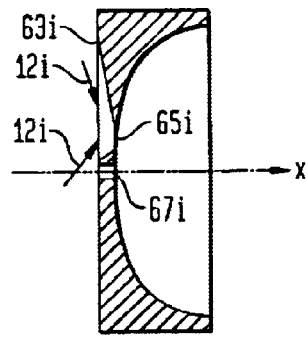
FIG. 6 is a cross-sectional view taken along line A—A of FIG. 4 of one of the half-sections of the resonator.
Figure 7:
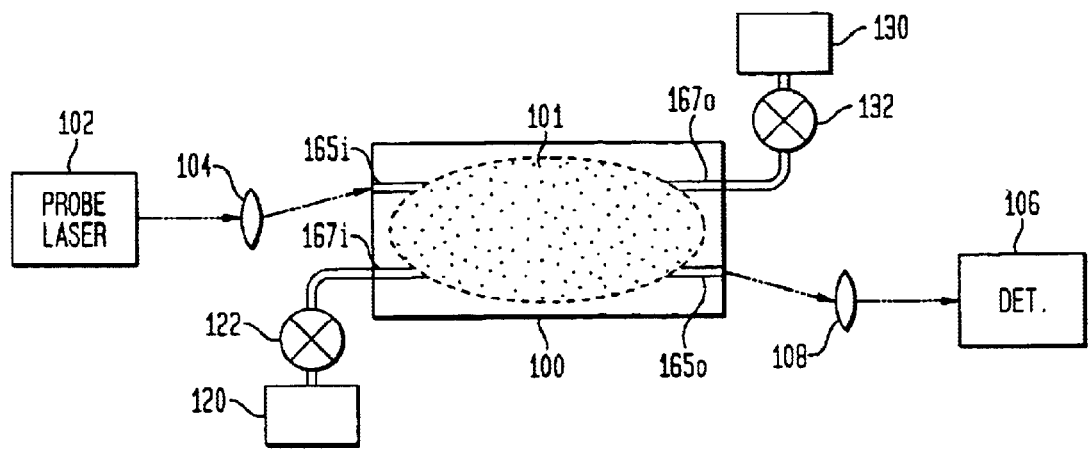
FIG. 7 is a block diagrammatic view of a trace gas sensing system in accordance with one application of our invention.
Figure 8:
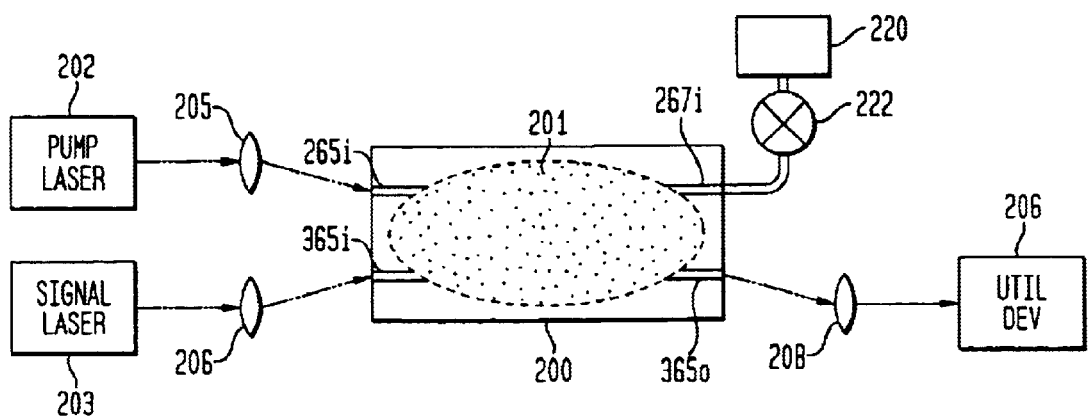
FIG. 8 is a block diagrammatic view of a high power laser system in accordance with another application of our invention.

The shape of a generic 2D quadrupole is defined in polar coordinates by the following expression:

$$r(\phi) \sim [1+(\epsilon/k)(\cos 2\phi)]_k \tag{1}$$

where k is a positive real number, and r, which can any real number as long as $r(\phi)>0$, is a deformation parameter that quantifies the degree to which the quadrupole is deformed from circular ($\epsilon=0$). Preferably $0<|\epsilon|<0.2$, but $|\epsilon|<0.2$ is not an absolute limit, rather a practical limit; that is, for $|\epsilon|>0.2$ the shape becomes nonconvex and thus more difficult to manufacture. To define a 3D shape suitable for the cavity of an optical resonator, the 2D quadrupole of equation (1) may be rotated about the x-axis of FIG. 1, thereby producing a resonator of the type shown in FIGS. 4–6. Depending on the sign of $\epsilon$, the resulting resonator will have the dimension along the axis of rotation either longer than the length in the perpendicular direction ($\epsilon$ positive; FIGS. 7–8) or shorter than the dimension in the perpendicular direction ($\epsilon$ negative; FIGS. 4–6).

Amongst other shapes, the 2D quadrupole is described by F. Capasso et al. in U.S. Pat. No. 6,134,257, supra. Likewise, the 2D quadrupole is also described by C. Grnachl et al. *Science*, supra and by, E. Narimanov et al., *Phys. Rev. Lett.*, supra.

EXAMPLE

With reference now to FIGS. 4–6, we show apparatus 60 that includes an optical cavity resonator of the type particularly suited to trace-gas sensing. The apparatus includes a pair of half-sections 62i and 62o assembled end-to-end to form a cavity resonator. Within the body the cavity resonator is a highly reflective surface so that it supports the propagation/circulation of optical rays therein along fully chaotic or quasi-chaotic ray paths, as discussed above. A plan view of section 62i is shown in FIG. 5. An optical input port 65i is located above the x-axis of rotation and is positioned within a scalloped section 63i that enables optical rays 12i (FIG. 6) to be coupled into the cavity resonator at shallow angles as well as at steep angles. Similarly, as shown in FIG. 4, an optical output port 65o is located within section 62o below the x-axis of rotation and is positioned within the scalloped section 63o.

In addition, the end faces include gas flow input and output ports 67i and 67o, respectively, which are depicted as preferably being located on the x-axis. In practice, these ports may also be located off the x-axis or combined into a single port at one location.

In accordance with the preceding sections, the shape of the resonator surface is determined, the phase space of the resonator of FIGS. 4–6 is calculated, the AZs and FZs are located in phase space, the type of input rays (chaotic, regular) are chosen, the optical ports 65i and 65o are positioned on the surface of the resonator at locations corresponding to AZs, and the gas ports 67i and 67o are positioned on the surface of the resonator at locations corresponding to FZs.

The drawings in FIGS. 4–6 are to scale with the outside diameter of cross-section A-A' measuring about 10 cm. The wall is about 5 mm thick at its thinnest region, all ports have hole diameters of about 5 mm, and the center-to-center distance between holes 67i and 65i (and 67o and 65o) is about 10 mm. With the given shape we can realize a total optical path length of several hundred meters. We designate the resonator length (e.g., about 10–50 cm) as the dimension measured along the y-axis in FIG. 1.

One feature of our invention combines the compactness of the resonator with the simultaneous capability of extremely long TOPLs (e.g., 100 s of meters to a few kilometers). Advantageously, the compactness of our resonators also provides for relatively rapid gas cycle times (e.g., 1 sec) since only a small gas volume has to be replaced after any measurement.

System Applications

As mentioned earlier, resonators in accordance with various embodiments of our invention find application in diverse systems; e.g., trace-gas sensing and optical amplification.

An illustrative trace-gas sensing system is shown in FIG. 7. It includes a chaotic resonator of the type described above including optical input and output ports 165i and 165o, respectively. A gaseous atmosphere (containing a suspected pollutant) is introduced into the resonator through gas input port 167 via input pump 120 and valve 122. After the measurement is complete, the atmosphere is exhausted through gas output port 167o via exhaust pump 130 and valve 132. (Alternatively, a single pump may be used to establish a continuous flow of the atmosphere through the resonator.) A wavelength-tunable probe laser 102 is coupled via a lens system 104 to optical input port 165i so that the laser beam enters the resonator at a direction that falls within a predetermined, desired range of input angles; i.e., those angles that produce the desired types of zones (i.e., FZs, AZs, or both), the desired type of ray paths (i.e., chaotic, regular, or both), and the desired long TOPLs, so that the various ports can be positioned following the principles set forth above. After circulating within the resonator, and being absorbed by the pollutant in the atmosphere, the beam exits via optical output port 165o. The exiting beam, which is amplitude modulated by the absorption, is incident on detector 106 via lens system 108. The output of the detector provides information as to the identity and concentration of the pollutant.

A high power laser system is illustrated in FIG. 8. The system includes a signal laser 203, an optical amplifier (pump laser 202, chaotic resonator 200, and gain medium 201) for amplifying the output of laser 203, and a utilization device for receiving the amplified output. The resonator 200 includes a gain medium 201, optical input ports 265i and 365i coupled via lens systems 205 and 206 to pump laser 202 and signal laser 203, respectively. In addition, the resonator includes an optical output port that is coupled via lens system 208 to utilization device 206.

If the gain medium is a fluid (gas or liquid), the resonator is also provided with a fluid port 267i coupled to a fluid pump 220 via a valve 222. If the gain medium is not a fluid (e.g., it is a solid state), then the port 267i and its associated pump may be omitted.

As in the trace-gas sensing system, both of the laser beams enter the resonator at directions that fall within a predetermined, desired range of input angles; i.e., those angles that produce the desired types of zones (i.e., FZs, AZs, or both), the desired type of ray paths (i.e., chaotic, regular, or both), and the desired long TOPLs, so that the various ports can be positioned following the principles set forth above.

In operation, the beams from both the pump laser 202 and the signal laser 203 simultaneously circulate within the resonator. The pump laser produces a population inversion throughout the gain medium, which amplifies the circulating beam from the signal laser. A significant feature of this system is that both beams circulate throughout the gain medium as extensively as possible without retracing themselves (i.e., the circulating paths are open paths), thereby reducing the likelihood of gain depletion and strongly amplifying the signal beam. To this end, we prefer that the density of the bounce points in the chaotic sea associated with the phase space of resonator 200 be essentially uniform or homogeneous.

It is to be understood that the above-described arrangements are merely illustrative of the many possible specific embodiments that can be devised to represent application of the principles of the invention. Numerous and varied other arrangements can be devised in accordance with these principles by those skilled in the art without departing from the spirit and scope of the invention.

Typically, in trace-gas sensing applications the optical rays that traverse our resonators are generated by lasers that emit at mid-infrared wavelengths. In such applications intersubband (ISB) lasers, including quantum cascade (QC) lasers, made from Group III–V compound semiconductors are preferred.

We claim:

1. A method of fabricating an optical resonator having at least one physical feature that communicates with the interior of the resonator, comprising the steps of:
   (a) selecting a 3D reflective, essentially closed surface such that optical rays reflected therefrom traverse paths that include chaotic, open paths;
   (b) determining the phase space of the reflection points of such rays as a function of the directions they enter the closed surface;
   (c) within the phase space identifying at least one forbidden zone where there are no such reflection points and at least one allowed zone where there are a multiplicity of such reflection points; and
   (d) forming the surface inside a rigid body, and
   (e) forming the at least one physical feature in a region of the surface determined by the position of the at least one forbidden zone or the at least one allowed zone.

2. The method of claim 1, wherein said physical feature comprises a gas port, and step (e) forms said gas port within a region of said surface that, in phase space, corresponds to said at least one forbidden zone and excludes said at least one allowed zone.

3. The method of claim 1, wherein said physical feature comprises an optical port, and step (e) forms said optical port within a region of said surface that, in phase space, corresponds to said at least one allowed zone.

4. The method of claim 3, wherein said allowed zone includes a chaotic sea of reflection points and said optical port is formed within a region of said surface that, in phase space, overlaps said chaotic sea.

5. The method of claim 3, wherein said phase space includes a chaotic sea of reflection points and at least one island formed therein, the boundary of said at least one island being formed by reflection points of rays that traverse regular optical paths, and said optical port is formed within a region of said surface that, in phase space, overlaps said at least one island.

6. The method of claim 5, wherein said physical feature comprises a gas port, and step (e) forms said gas port within a region of said surface that, in phase space, lies within said chaotic sea.

7. The method of claim 1, wherein said 3D surface is formed by a 2D surface of revolution about a predetermined axis.

8. The method of claim 7, wherein said physical feature comprises a gas port, and step (e) forms said gas port near to said axis.

9. The method of claim 7, wherein said 2D surface is a flattened quadrupole.

10. The method of claim 1, wherein said 3D surface is aspherical.

11. Apparatus comprising:
    a rigid body having at least one optical port coupled to a closed optical resonator, said resonator being located within said body and being formed by a reflective surface, the port enabling optical input rays to enter said resonator in different directions,
    the shape of said surface being such that optical rays reflected therefrom traverse paths that include chaotic, open paths and have a characteristic phase space of optical ray reflection points, said shape being designed so that said phase space has at least one forbidden zone where there are no such reflection points for said input rays and at least one allowed zone where there are a multiplicity of such reflection points for said input rays, and
    said at least one optical port is located in a region of said surface that, in phase space, corresponds to said at least one allowed zone.

12. The apparatus of claim 11, wherein said body has at least one gas port coupled to said resonator, said at least one gas port being located in a region of said surface that, in phase space, corresponds to said at least one forbidden zone.

13. The apparatus of claim 11, further including means for introducing optical rays into said resonator along angles that cause said rays to propagate along chaotic paths, wherein said allowed zone includes a chaotic sea of reflection points, and said at least one optical port is formed within a region of said surface that, in phase space, overlaps said chaotic sea.

14. The apparatus of claim 11, further including means for introducing optical rays into said resonator along angles that cause said rays to propagate along regular paths, wherein said phase space includes a chaotic sea of reflection points and at least one island formed therein, the boundary of said at least one island being formed by reflection points of rays that traverse regular optical paths, and said optical port is formed within a region of said surface that, in phase space, overlaps said at least one island.

15. The apparatus of claim 14, wherein said body has at least one gas port coupled to said resonator, said at least one gas port being located in a region of said surface that, in phase space, corresponds to said chaotic sea.

16. The apparatus of claim 11, wherein said 3D surface is formed by a 2D surface of revolution about a predetermined axis.

17. The apparatus of claim 16, wherein said body has at least one gas port coupled to said resonator, said at least one gas port being located in a region of said surface that is near to said axis.

18. The apparatus of claim 16, wherein said 2D surface is a flattened quadrupole.

19. The apparatus of claim 11, wherein said 3D surface is aspherical.

20. A trace-gas detection system comprising apparatus according to claim 12 for containing a gaseous atmosphere that includes said trace gas, said atmosphere introduced to said resonator through said gas port, optical input and output ports coupled to said resonator, said optical ports being positioned according to claim 12,
- a probe laser coupled to said input port for introducing said optical rays into said resonator, said optical rays having a wavelength such that they are absorbed by said trace gas, and
- a detector for detecting said rays after they exit said resonator through said output optical port.

21. A laser system comprising apparatus according to claim 11 for containing an optical gain medium,
- optical input and output ports coupled to said resonator and positioned according to claim 11,
- a pump laser coupled to an optical input port for producing a population inversion in said gain medium,
- a signal laser coupled to an optical input port for introducing into said resonator a signal rays for amplification by said gain medium, and
- utilization means coupled to an optical output port for receiving said amplified signal rays.

* * * * *